(12) United States Patent
Chu (10) Patent No.: US 10,856,944 B2
(45) Date of Patent: Dec. 8, 2020

(54) TRIAXIAL MOTION DEVICE

(71) Applicant: Hiwin Technologies Corp., Taichung (TW)

(72) Inventor: Yu-Lin Chu, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 112 days.

(21) Appl. No.: 16/180,152

(22) Filed: Nov. 5, 2018

(65) Prior Publication Data

US 2020/0138528 A1 May 7, 2020

(51) Int. Cl.
| | |
|---|---|
| *A61B 34/30* | (2016.01) |
| *A61B 34/00* | (2016.01) |
| *F16H 19/00* | (2006.01) |
| *B25J 9/04* | (2006.01) |
| *B25J 9/10* | (2006.01) |

(Continued)

(52) U.S. Cl.
CPC ............. *A61B 34/30* (2016.02); *A61B 34/71* (2016.02); *B25J 9/042* (2013.01); *B25J 9/046* (2013.01); *B25J 9/104* (2013.01); *B25J 9/1015* (2013.01); *B25J 9/126* (2013.01); *B25J 18/007* (2013.01); *F16H 19/005* (2013.01)

(58) Field of Classification Search
CPC ... A61B 2034/305; B25J 9/1015; B25J 9/104; B25J 15/0425; B25J 18/007; B25J 9/042; B25J 9/046; B25J 9/126; B23Q 5/20
See application file for complete search history.

(56) References Cited

U.S. PATENT DOCUMENTS

| | | | | |
|---|---|---|---|---|
| 5,132,601 A | * | 7/1992 | Ohtani | ............ B25J 9/046 318/567 |
| 2010/0252292 A1 | * | 10/2010 | Pyles | .......... B24B 23/022 173/164 |

(Continued)

FOREIGN PATENT DOCUMENTS

| | | |
|---|---|---|
| CN | 104626129 A | 5/2015 |
| CN | 108466257 A | 8/2018 |

(Continued)

OTHER PUBLICATIONS http://mechanicallec.blogspot.com/2017/04/machine-design-belt-drive-4.html?spref=pi(Apr. 9, 2017.).

*Primary Examiner* — Joseph Brown
(74) *Attorney, Agent, or Firm* — Muncy, Geissler, Olds & Lowe, P.C.

(57) ABSTRACT

A triaxial motion device includes first, second and third bases, first and second power sources, and a workpiece positioning member. The first power source is disposed on the first base and has a first driving shaft. The second base is connected with the first driving shaft through a cannular rotary shaft in a way that the second base is rotatable about a first axis. The second power source is disposed on the first base and has a second driving shaft penetrating through the cannular rotary shaft. The third base is connected with the second driving shaft in a way that the third base is rotatable about a second axis perpendicular to the first axis. The workpiece positioning member is disposed on the third base and rotatable about a third axis perpendicular to the second axis. Therefore, the triaxial motion device has small volume and performs highly precise motion.

13 Claims, 9 Drawing Sheets

(51) Int. Cl.
*B25J 9/12* (2006.01)
*B25J 18/00* (2006.01)

(56) References Cited

U.S. PATENT DOCUMENTS

| | | | | |
|---|---|---|---|---|
| 2012/0034022 | A1* | 2/2012 | Long | B25J 17/0258 403/81 |
| 2013/0081502 | A1* | 4/2013 | Long | B25J 17/0258 74/490.04 |
| 2013/0118288 | A1* | 5/2013 | Liu | B25J 17/0258 74/490.04 |

FOREIGN PATENT DOCUMENTS

| | | |
|---|---|---|
| DE | 8807583 U1 | 11/1989 |
| DE | 10032098 A1 | 1/2002 |
| DE | 102009018917 A1 | 11/2010 |
| DE | 102014105775 B4 | 3/2016 |
| DE | 102017217907 A1 | 4/2019 |
| EP | 0080325 B1 | 6/1986 |
| JP | H4-152090 A | 5/1992 |
| KR | 1997-0001660 B1 | 2/1997 |
| KR | 10-2017-0124245 A | 11/2017 |
| KR | 10-2017-0143396 A | 12/2017 |

\* cited by examiner

TRIAXIAL MOTION DEVICE

BACKGROUND OF THE INVENTION

1. Field of the Invention

The present invention relates to multiaxial motion devices and more particularly, to a triaxial motion device which is small in volume thereof and movable with high precision.

2. Description of the Related Art

Presently, surgical robots have been widely used in various kinds of surgical operations. With the assistance of the surgical robot, the surgeon can precisely handle many operation-related medical treatments such as verifying the position of lesion or controlling the depth of cut, so that any latent medical risk resulted from artificially operational negligence can be significantly lowered. However, the presently available surgical robots have the disadvantage of huge volume, and therefore should be operated in relatively larger space.

SUMMARY OF THE INVENTION

It is a primary objective of the present invention to provide a triaxial motion device which is capable of performing highly precise motion with multi-degree of freedom and applicable to a surgical robot to make the surgical robot have small volume.

To attain the above-mentioned primary objective, the triaxial motion device of the present invention includes a first base, a cannular rotary shaft, a first power source, a second base, a second power source, a third base, and a rotary unit. The first power source is disposed on the first base and has a first driving shaft. The cannular rotary shaft is connected with the first driving shaft in a way that the cannular rotary shaft is capable of being driven by the first driving shaft of the first power source to rotate synchronously with the first driving shaft. The second base is connected with the cannular rotary shaft in a way that the second base is capable of being driven by the cannular rotary shaft to rotate relative to the first base about a first axis. The second power source is disposed on the first base and has a second driving shaft rotatably penetrating through the cannular rotary shaft. The third base is connected with the second driving shaft of the second power source in a way that the third base is capable of being driven by the second driving shaft of the second power source to rotate relative to the second base about a second axis perpendicular to the first axis. The rotary unit is disposed on the third base and has a workpiece positioning member rotatable relative to the third base about a third axis perpendicular to the second axis.

It can be known from the above description that the triaxial notion device of the present invention can perform highly precise motion with multi-degree of freedom, thereby applicative to the surgical robot specialized in minimally invasive surgery for ear and nose. Besides, the surgical robot applied with the present invention has the advantage of small volume, thereby prevented from the conventional surgical robot's disadvantage of huge volume and high weight.

Preferably, the first driving shaft is parallel to the first axis, and the second driving shaft is coaxial with the first axis. In this way, the power loss during the transmission is reduced.

Preferably, the first and second power sources are located on a same side of the first base. In this way, the members with large volume are gathered together, that can minimize the volume of the triaxial motion device.

Preferably the first base has a first arm and a second arm, an end of the first arm is connected with an end of the second arm, and the included angle between the first and second arms is ranged from 90 to 180 degrees. In this way, during the operation there is sufficient space for the first base to avoid the object thereunder, such as the head or other body parts of the patient.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

First of all, it is to be mentioned that same reference numerals used in the following preferred embodiments and the appendix drawings designate same or similar elements throughout the specification for the purpose of concise illustration of the present invention.

Figure 1:
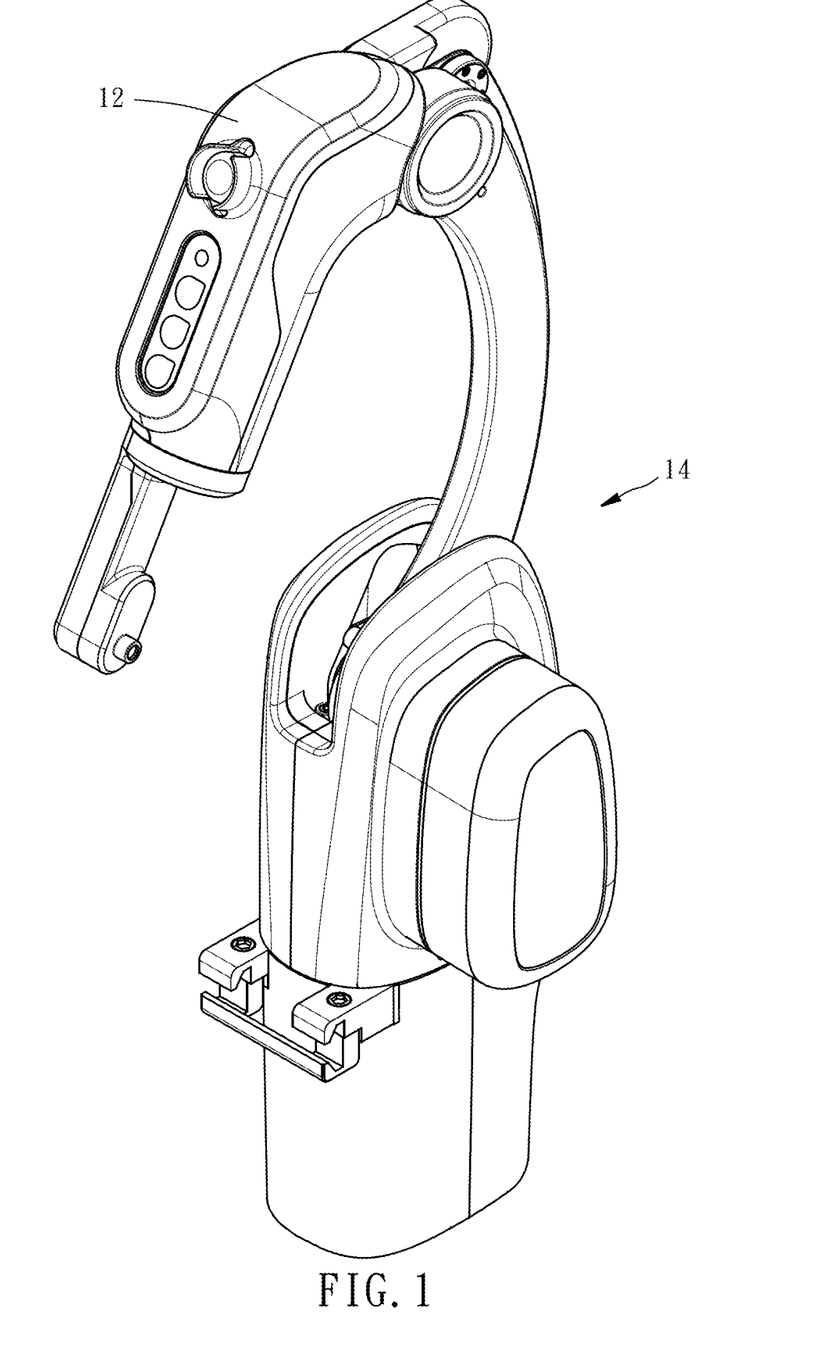
FIG. 1 is a perspective view showing the appearance of a surgical robot applied with the triaxial motion device of the present invention.
Figure 2:
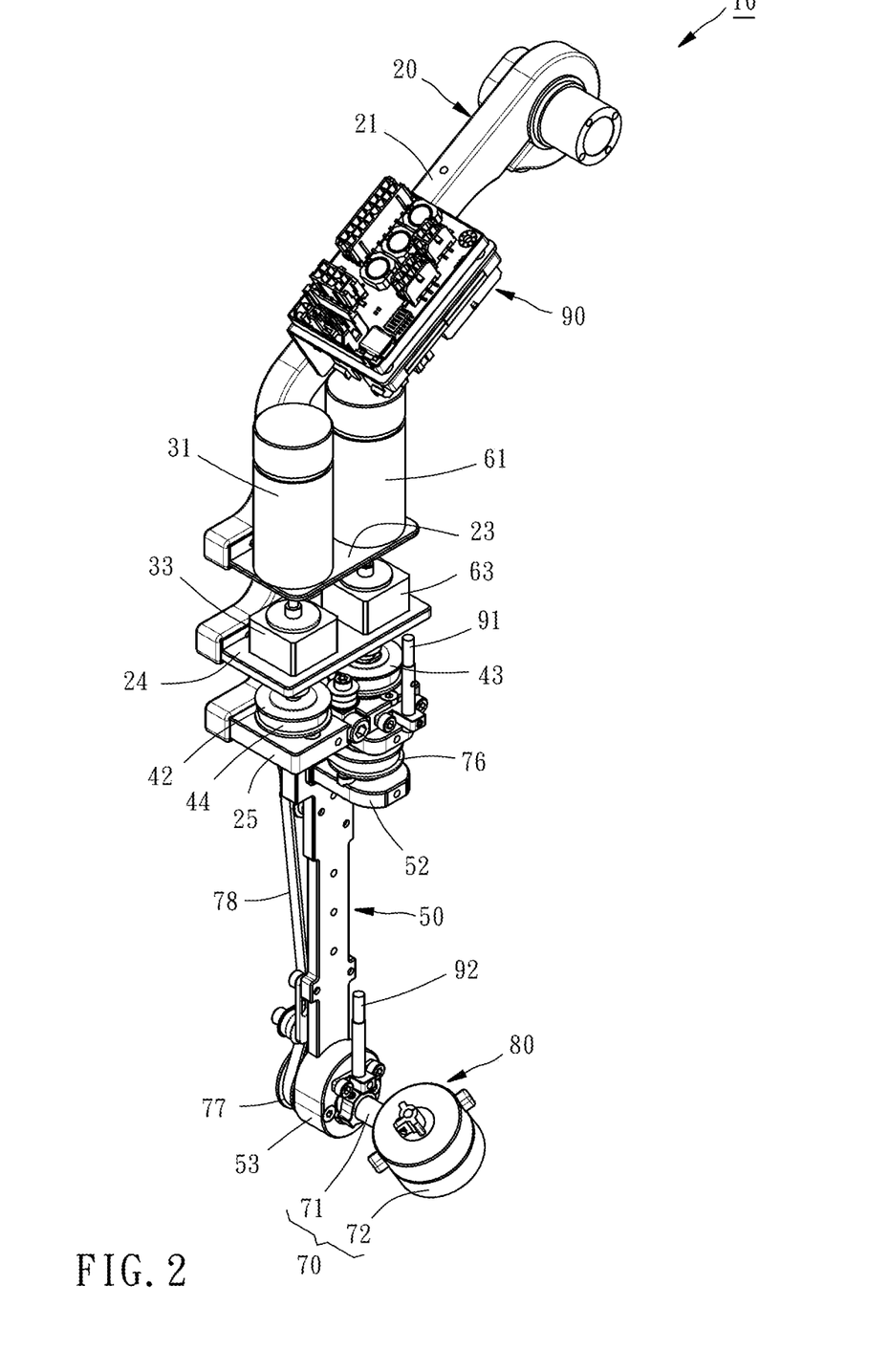
FIG. 2 is a perspective view of the triaxial motion device of the present invention.
Figure 3:
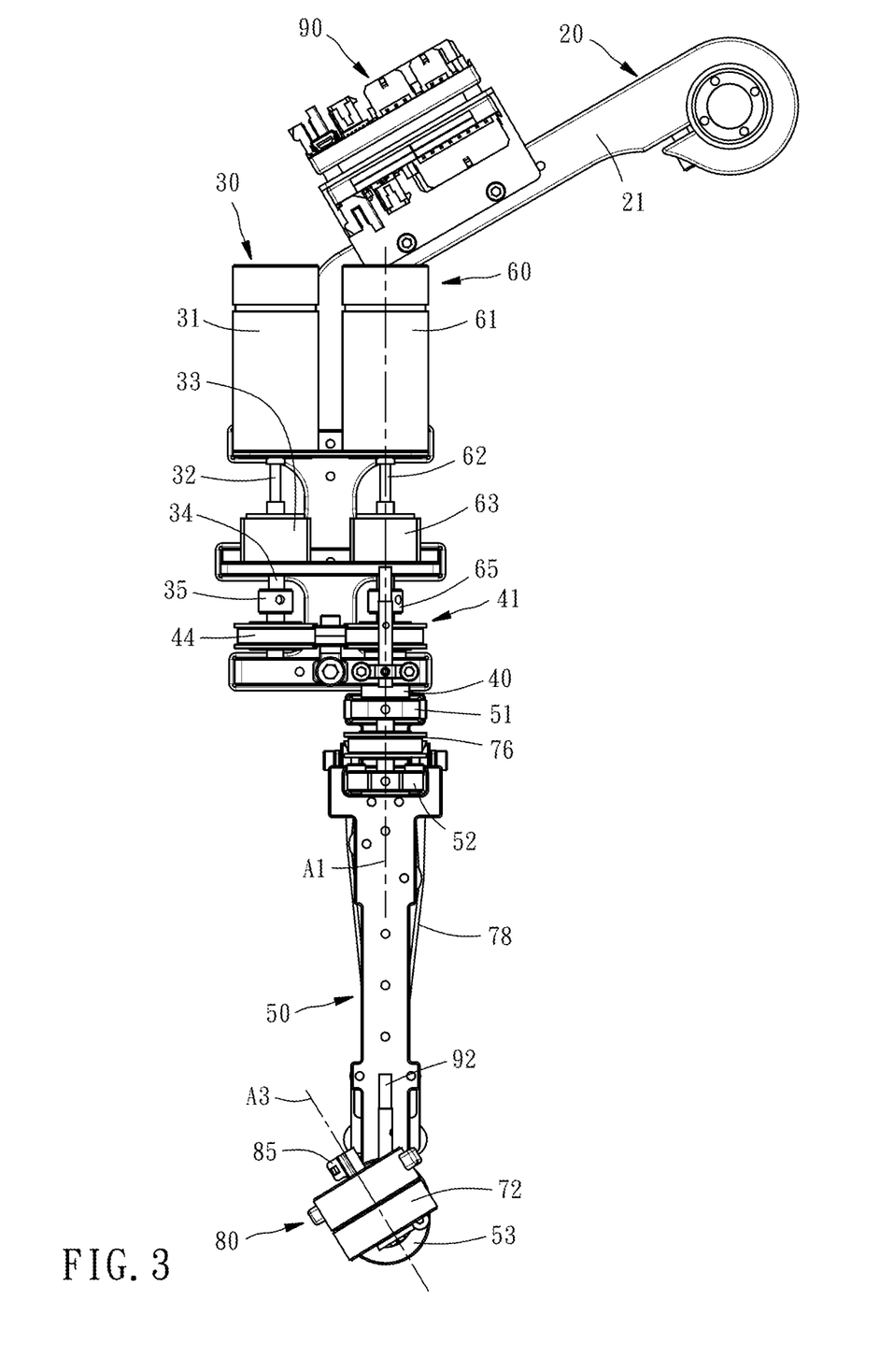
FIG. 3 is a front view of the triaxial motion device of the present invention.

Referring to FIG. 1, FIG. 1 shows the configuration that a triaxial motion device 10 of the present invention is installed in a case 12 and then applied to a surgical robot 14. Referring to FIGS. 2 and 3, FIGS. 2 and 3 show the configuration of the triaxial motion device 10 of the present invention after the case 12 is removed. The triaxial motion device 10 primarily includes a first base 20, a first power source 30, a cannular rotary shaft 40, a second base 50, a second power source 60, a third base 70, and a rotary unit 80.

Figure 4:
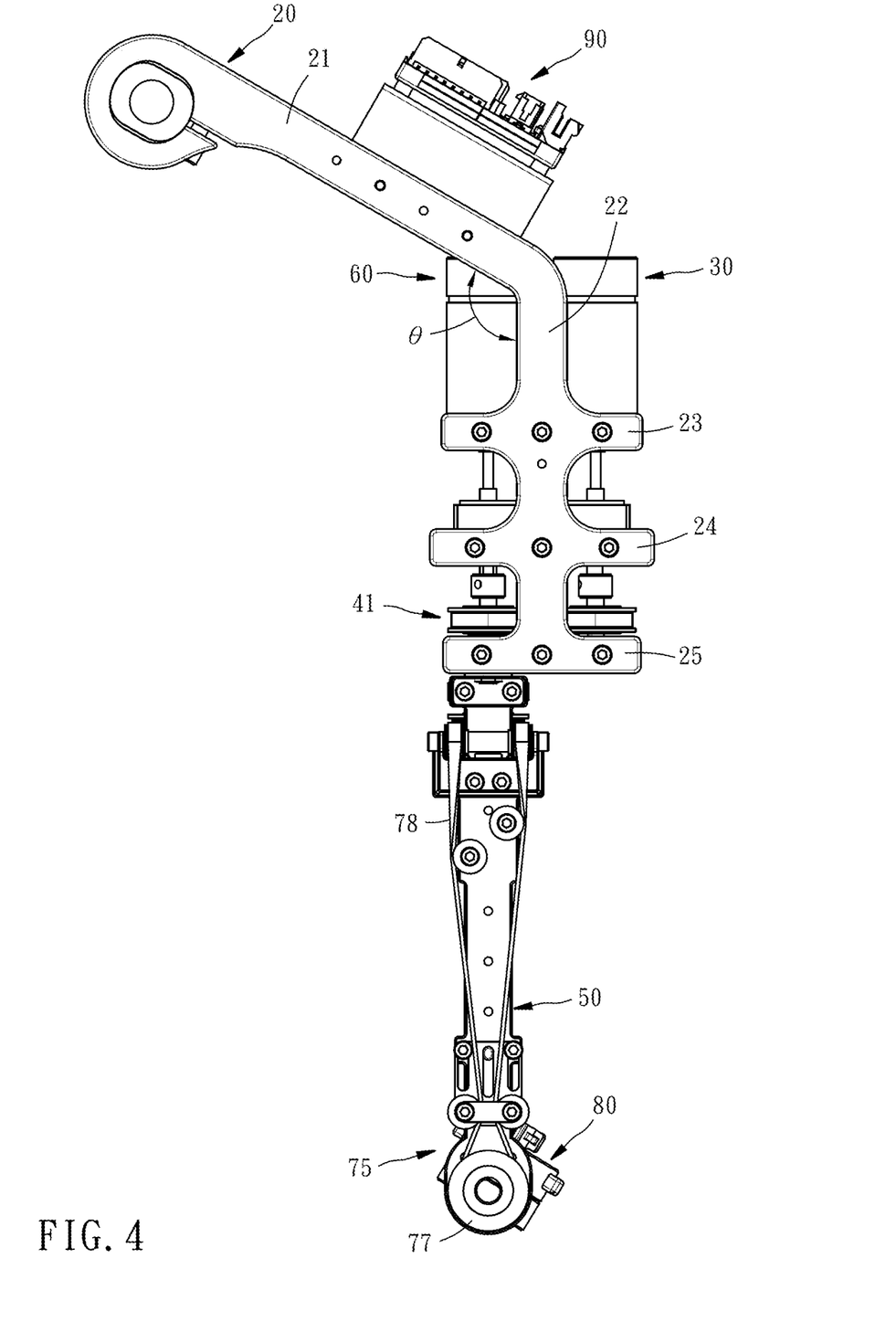
FIG. 4 is a rear view of the triaxial motion device of the present invention.

The first base 20 has a first arm 21 and a second arm 22. The bottom end of the first arm 21 is integrally connected with the top end of the second arm 22, and the included angle θ between the first and second arms 21 and 22 is ranged from 90 to 180 degrees, as shown in FIG. 4. Because of such included angle θ, during the operation there is sufficient space for the first base 20 to avoid the object thereunder, such as the head or other body parts of the patient, so that the present invention is applicative to the surgical robot specialized in minimally invasive surgery for ear and nose. Besides, as shown in FIGS. 2 and 4, the first arm 21 is adapted for a controller 90 to be fixedly installed thereon. The second arm 22 is provided from the top to the bottom thereof with a first supporting plate 23, a second supporting plate 24 and a third supporting plate 25 in order.

Figure 6:
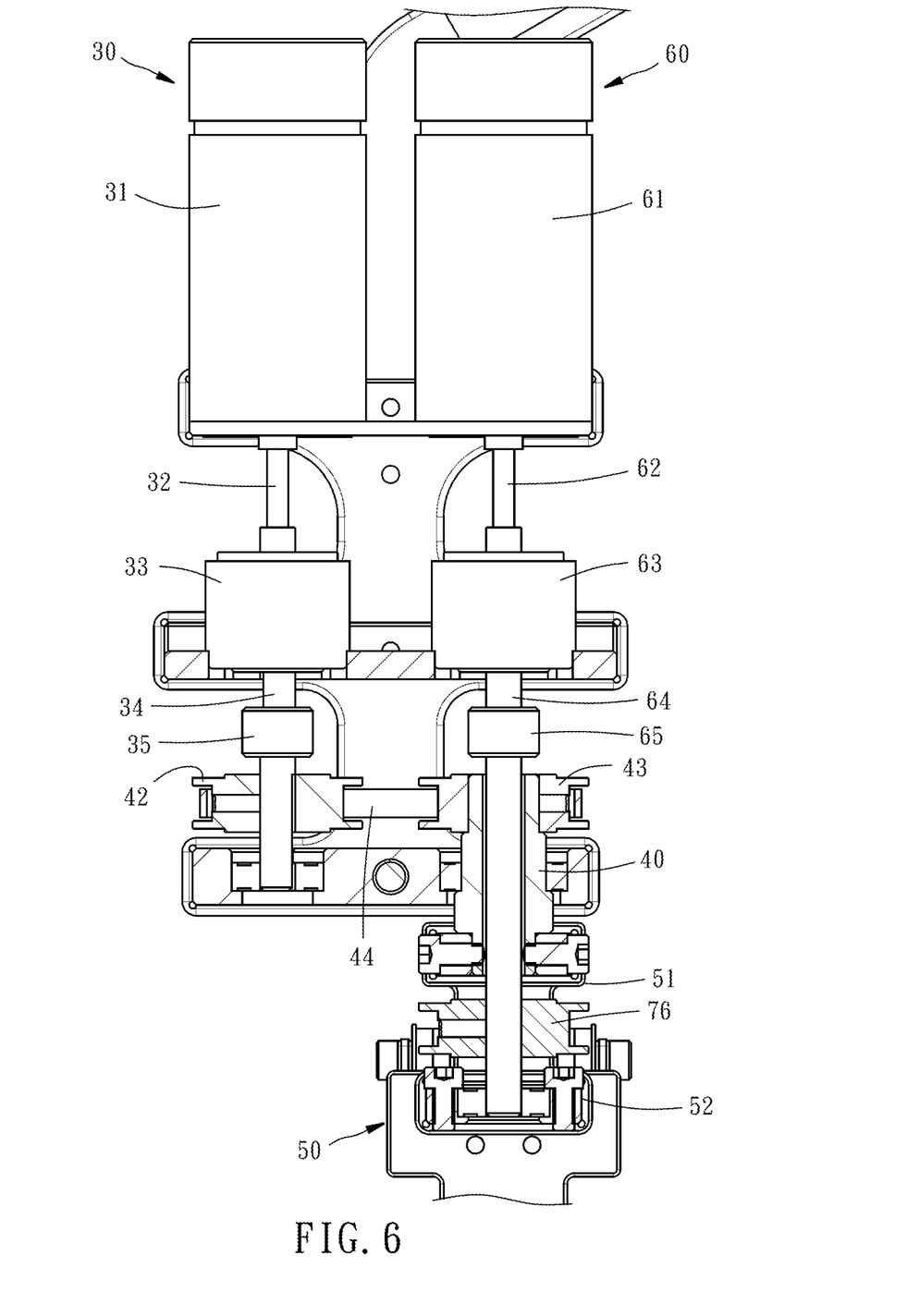
FIG. 6 is a partially sectional view of the triaxial motion device of the present invention.

The first power source 30 has a first motor 31, a first decelerator 33 and a first driving shaft 35. The first motor 31 is disposed on the first supporting plate 23 of the second arm 22 of the first base 20 and has a first outputting shaft 32. The first decelerator 33 is disposed on the second supporting plate 24 of the second arm 22 of the first base 20 and has a first transmission shaft 34. As shown in FIGS. 3 and 6, the first outputting shaft 32 of the first motor 31 is connected with the first decelerator 33, and the first transmission shaft 34 of the first decelerator 33 is connected with the first driving shaft 35 coaxially, so that the first driving shaft 35 can be driven by the first motor 31 to rotate.

The cannular rotary shaft 40 rotatably penetrates through the third supporting plate 25 of the second arm 22 of the first base 20 and is connected with the first driving shaft 35 of the first power source 30 through a first transmission unit 41. Specifically speaking, as shown in FIGS. 2, 3 and 6, the first transmission unit 41 has a first transmission pulley 42, a second transmission pulley 43 and a first transmission belt 44. The first transmission pulley 42 is disposed on the third supporting plate 25 of the second arm 22 of the first base 20 and connected with the first driving shaft 35 coaxially. The second transmission pulley 43 is disposed on the third supporting plate 25 of the second arm 22 of the first base 20 and connected with the cannular rotary shaft 40 coaxially. The first transmission belt 44 is wound around the first and second transmission pulleys 42 and 43 to enable the first and second transmission pulleys 42 and 43 to rotate synchronously.

As a result, the first driving shaft 35 of the first power source 30 drives the first transmission pulley 42 to rotate, the first transmission pulley 42 drives the second transmission pulley 43 to rotate through the first transmission belt 44, and the second transmission pulley 43 drives the cannular rotary shaft 40 to rotate together.

Figure 5:
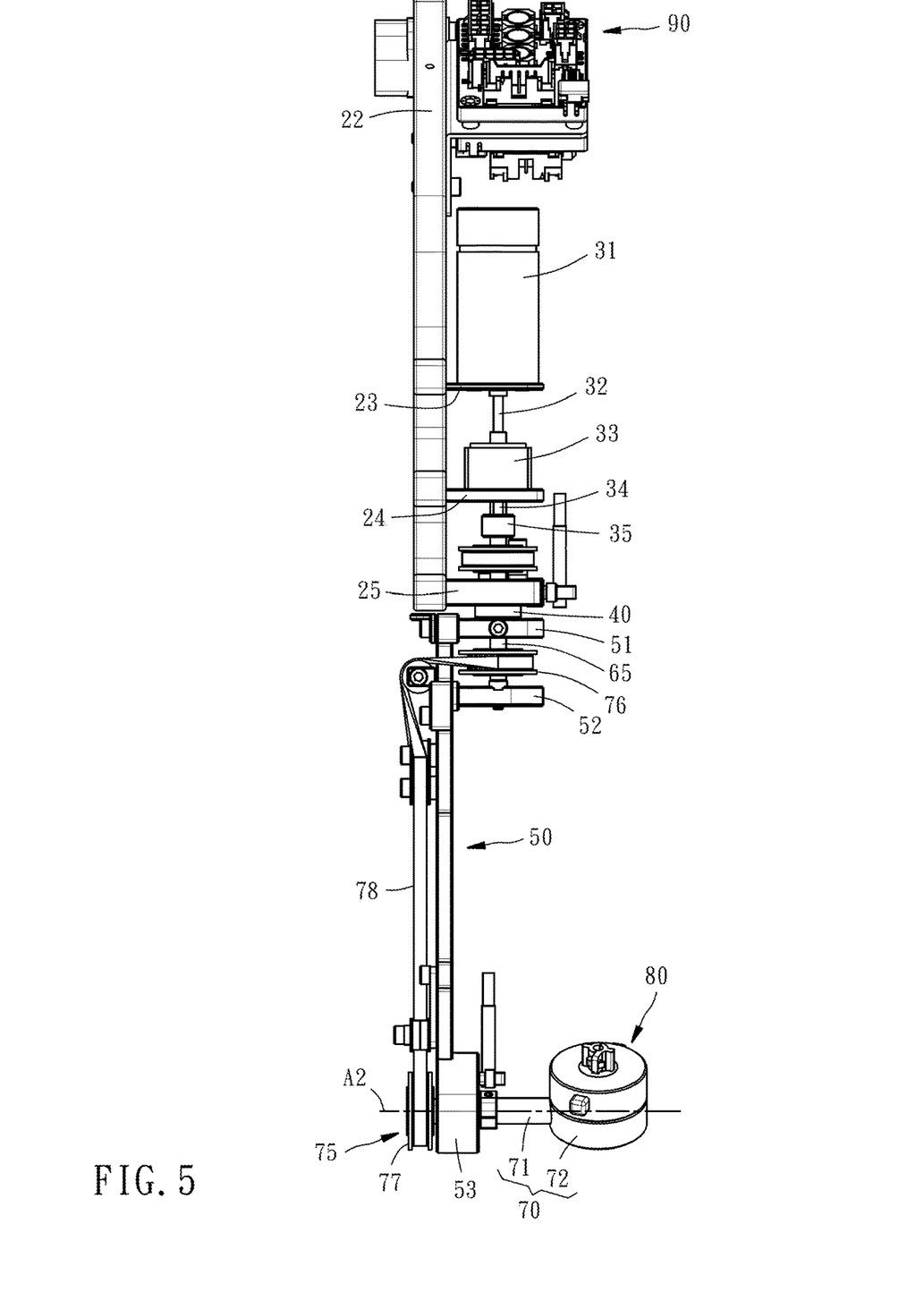
FIG. 5 is a lateral view of the triaxial motion device of the present invention.

The second base 50 is located under the first base 20. As shown in FIGS. 3 and 5, the second base 50 is provided on the top end thereof with a fourth supporting plate 51 and a fifth supporting plate 52 located below the fourth supporting plate 51. The second base 50 is provided on the bottom end thereof with a disc portion 53. As shown in FIGS. 3 and 6, the fourth supporting plate 51 of the second base 50 is connected with the bottom end of the cannular rotary shaft 40 coaxially in a way that the second base 50 can be driven by the cannular rotary shaft 40 to rotate relative to the first base 20 about a first axis A1. The first axis A1 is parallel to the first driving shaft 35 of the first power source 30. Besides, the rotary angle of the second base 50 can be sensed by a first angular sensor 91 as shown in FIG. 2. The first angular sensor 91 is disposed on the third supporting plate 25 of the second arm 22 of the first base 20 and electrically connected with the controller 90, so that the sensing result of the first angular sensor 91 can be transmitted to the controller 90 for estimation.

The second power source 60 and the first power source 30 are located on a same side of the first base 20. The second power source 60 has a second motor 61, a second decelerator 63, and a second driving shaft 65. The second motor 61 is disposed on the first supporting plate 23 of the second arm 22 of the first base 20 and has a second outputting shaft 62. The second decelerator 63 is disposed on the second supporting plate 24 of the second arm 22 of the first base 20 and has a second transmission shaft 64. As shown in FIGS. 3 and 6, the second outputting shaft 62 of the second motor 61 is connected with the second decelerator 63, the second transmission shaft 64 of the second decelerator 63 is connected with the second driving shaft 65 coaxially, and the second driving shaft 65 penetrates through the cannular rotary shaft 40 coaxially with the first axis A1 in a way that the second driving shaft 65 can be driven by the second motor 61 to rotate relative to the cannular rotary shaft 40.

The third base 70 has an axial portion 71 penetrating through the disc portion 53 of the second base 50 and is connected with the second driving shaft 65 of the second power source 60 through a second transmission unit 75. Specifically speaking, as shown in FIGS. 4-6, the second transmission unit 75 has a third transmission pulley 76, a fourth transmission pulley 77 and a second transmission belt 78. The third transmission pulley 76 is disposed on the fifth supporting plate 52 of the second base 50 and connected with the second driving shaft 65 of the second power source 60 coaxially. The fourth transmission pulley 77 is disposed on the back surface of the disc portion 53 of the second base 50 and connected with the axial portion 71 of the third base 70 coaxially. The second transmission belt 78 connects the third and fourth transmission pulleys 76 and 77 to enable the third and fourth transmission pulleys 76 and 77 to rotate synchronously.

As a result, the second driving shaft 65 of the second power source 60 drives the third transmission pulley 76 to rotate, the third transmission pulley 76 drives the fourth transmission pulley 77 to rotate through the second transmission belt 78, and the fourth transmission pulley 77 drives the third base 70 to rotate relative to the second base 50 about a second axis A2 perpendicular to the first axis A1. Besides, the rotary angle of the third base 70 can be sensed by a second angular sensor 92. As shown in FIGS. 2 and 3, the second angular sensor 92 is disposed on the disc portion 53 of the second base 50 and electrically connected with the controller 90, so that the sensing result of the second angular sensor 92 can be transmitted to the controller 90 for estimation.

Figure 7:
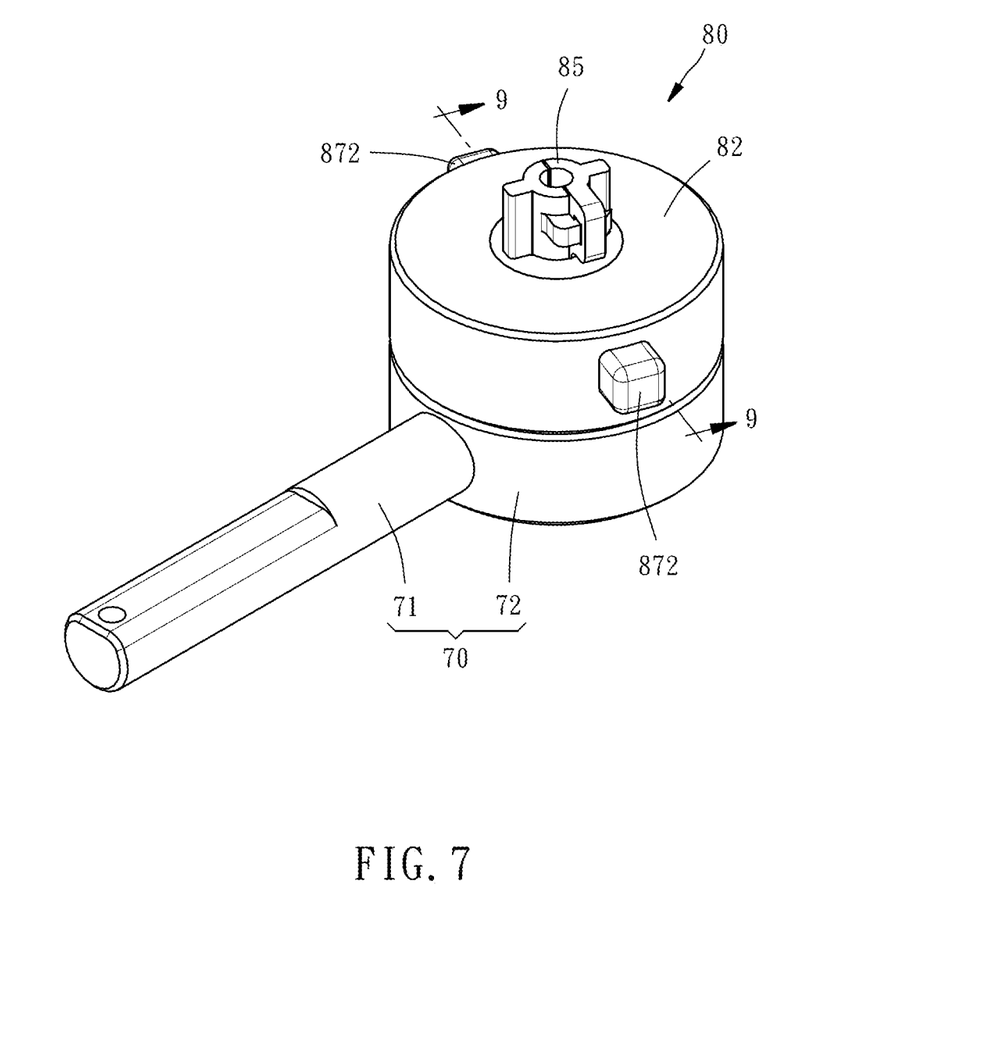
FIG. 7 is an assembled perspective view of a third base and a rotary unit of the triaxial motion device of the present invention.
Figure 8:
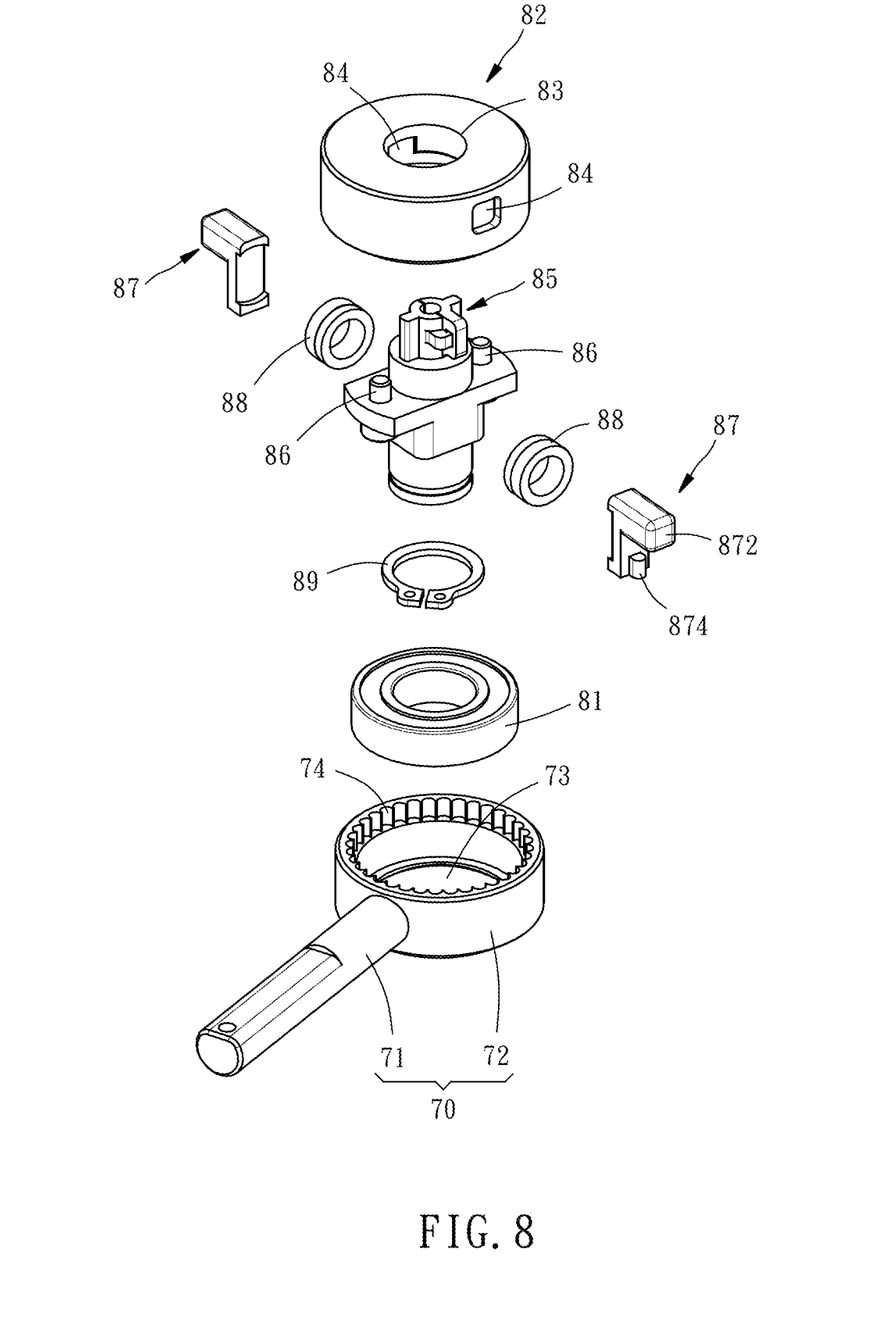
FIG. 8 is an exploded perspective view of the third base and the rotary unit of the triaxial motion device of the present invention.
Figure 9:
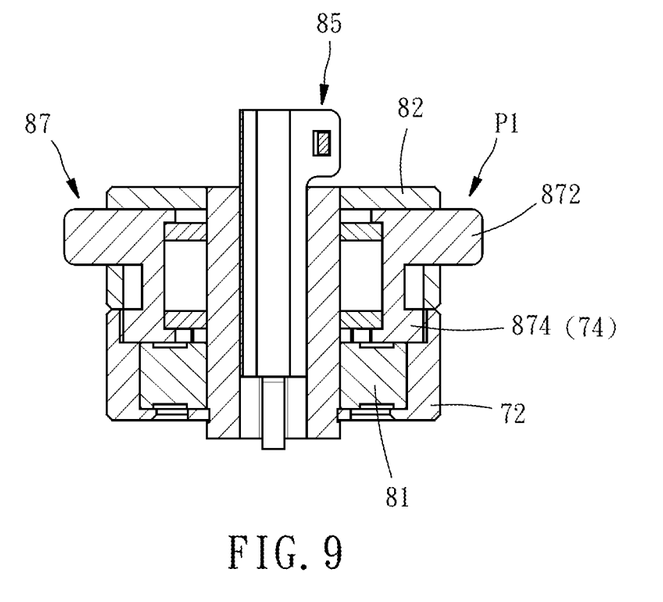
FIG. 9 is a sectional view taken along the line 9-9 in FIG. 7, primarily showing that keys are located at a first position.
Figure 10:
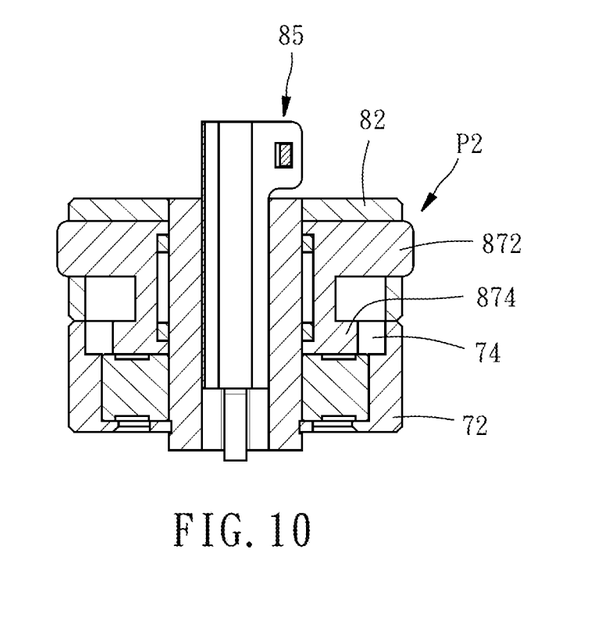
FIG. 10 is similar to FIG. 9, but primarily showing that the keys are located at a second position.

In addition, as shown in FIGS. 7 and 8, the third base 70 further has a seat 72 connected with the axial portion 71. The seat 72 has an accommodating recess 73. The accommodating recess 73 is provided on the inner wall thereof with a plurality of positioning grooves 74. The rotary unit 80 has a bearing 81, a top cap 82, a workpiece positioning member 85, two keys 87, and two elastic members 88. The bearing 81 is disposed in the accommodating recess 73. The top cap 82 covers the accommodating recess 73 and has a top hole 83 axially communicating with the accommodating recess 73 and two key holes 84 opposite to each other and radially communicating with the accommodating recess 73. The workpiece positioning member 85 is fastened to the top cap 82 by fastening members 86 such as screws, primarily for a workpiece, such as a laparoscope, to be installed and positioned on the workpiece positioning member 85. The top end of the workpiece positioning member 85 protrudes out of the top hole 83. The bottom end of the workpiece positioning member 85 is fastened to the bearing 81 by a buckle 89. The key 87 is disposed in the top cap 82 and provided with a pressed portion 872 and a positioning portion 874. The pressed portion 872 is inserted in the key hole 84 of the top cap 82. The positioning portion 874 is located correspondingly to one of the positioning grooves 74. When the pressed portion of the key 87 is not applied with an external force and therefore the key 87 is located at a first position P1 as shown in FIG. 9, the positioning portion 874 of the key 87 is engaged in one of the positioning grooves 74 of the third base 70, thereby disabling the rotary unit 80 to rotate relative to the third base 70. When the pressed portion 872 of the key 87 is applied with an external force and therefore the key 87 is forced to be located at a second position P2 as shown in FIG. 10, the positioning portion 874 of the key 87 is separated from the positioning groove 74 engaged therewith formerly, thereby enabling the rotary unit 80 to rotate relative to the third base 70 about a third axis A3 perpendicular to the second axis A2. The elastic member 88 is disposed between the workpiece positioning member 85 and the key 87 for keeping the key 87 located at the first position P1 as shown in FIG. 9.

It can be known from the above description that in the triaxial motion device 10 of the present invention, the second base 50, the third base 70 and the rotary unit 80 are rotatable about different axis respectively, so that the present invention is convenient to adjust the position of the workpiece according to the practical demands and applicative to the surgical robot specialized in minimally invasive surgery for ear and nose. Besides, the large-volume members of the triaxial motion device 10 of the present invention, such as the first and second power sources 30 and 60, are gathered together on the same side, that is effective in minimizing the volume of the surgical robot applied with the present invention.

What is claimed is:

1. A triaxial motion device comprising:
    a first base having a first arm and a second arm having an end connected with an end of the first arm; wherein the second arm is provided from a top to a bottom thereof with a first supporting plate, a second supporting plate and a third supporting plate in order;
    a first power source having a first motor, a first decelerator and a first driving shaft, wherein the first motor is disposed on the first supporting plate and has a first outputting shaft connected with the first decelerator; the first decelerator is disposed on the second supporting plate and has a first transmission shaft connected with the first driving shaft coaxially;
    a cannular rotary shaft rotatably penetrating through the third supporting plate and connected with the first driving shaft of the first power source in a way that the cannular rotary shaft is capable of being driven by the first driving shaft to rotate synchronously with the first driving shaft;
    a second base connected with the cannular rotary shaft in a way that the second base is capable of being driven by the cannular rotary shaft to rotate relative to the first base about a first axis;
    a second power source disposed on the first base and having a second driving shaft rotatably penetrating through the cannular rotary shaft;
    a third base connected with the second driving shaft of the second power source in a way that the third base is capable of being driven by the second driving shaft of the second power source to rotate relative to the second base about a second axis perpendicular to the first axis; and
    a rotary unit disposed on the third base and having a workpiece positioning member rotatable relative to the third base about a third axis perpendicular to the second axis.

2. The triaxial motion device as claimed in claim 1, wherein the first power source and the second power source are located on a same side of the first base.

3. The triaxial motion device as claimed in claim 2, wherein the first driving shaft of the first power source is connected with the cannular rotary shaft through a first transmission unit; the first transmission unit has a first transmission pulley, a second transmission pulley and a first transmission belt; the first transmission pulley is disposed on the first base and connected with the first driving shaft coaxially; the second transmission pulley is disposed on the first base and connected with the cannular rotary shaft coaxially; the first transmission belt is wound around the first transmission pulley and the second transmission pulley.

4. The triaxial motion device as claimed in claim 2, wherein the second driving shaft of the second power source is connected with the third base through a second transmission unit; the second transmission unit has a third transmission pulley, a fourth transmission pulley and a second transmission belt; the third transmission pulley is disposed on a top end of the second base and connected with the second driving shaft coaxially; the fourth transmission pulley is disposed on a bottom end of the second base and connected with the third base; the second transmission belt is wound around the third transmission pulley and the fourth transmission pulley.

5. The triaxial motion device as claimed in claim 4, wherein the second power source further has a second motor and a second decelerator; the second motor has a second outputting shaft connected with the second decelerator; the second decelerator has a second transmission shaft connected with the second driving shaft coaxially.

6. The triaxial motion device as claimed in claim 2, wherein an included angle between the first arm and the second arm is ranged from 90 to 180 degrees; the first power source and the second power source are both disposed on the second arm.

7. The triaxial motion device as claimed in claim 1, wherein the first driving shaft is parallel to the first axis.

8. The triaxial motion device as claimed in claim 7, wherein the second driving shaft is coaxial with the first axis.

9. The triaxial motion device as claimed in claim 1, wherein the third base has an accommodating recess; the rotary unit further has a bearing, a top cap, a key and an elastic member; the bearing is disposed in the accommodating recess; the top cap covers the accommodating recess and has a top hole axially communicating with the accommodating recess and a key hole radially communicating with the accommodating recess; the workpiece positioning member is disposed on the top cap; a top end of the workpiece positioning member protrudes out of the top hole; a bottom end of the workpiece positioning member is connected with the bearing; the key is disposed in the key hole of the top cap movably between a first position and a second position; when the key is located at the first position, the key is positioned on the third base to disable the rotary unit to rotate relative to the third base; when the key is located at the second position, the key is separated from the third base to enable the rotary unit to rotate relative to the third base; the elastic member is disposed between the workpiece positioning member and the key for keeping the key located at the first position.

10. The triaxial motion device as claimed in claim 1, wherein the second driving shaft is coaxial with the first axis.

11. The triaxial motion device as claimed in claim 1, wherein the first driving shaft of the first power source is connected with the cannular rotary shaft through a first transmission unit; the first transmission unit has a first transmission pulley, a second transmission pulley and a first transmission belt; the first transmission pulley is disposed on the first base and connected with the first driving shaft coaxially; the second transmission pulley is disposed on the first base and connected with the cannular rotary shaft coaxially; the first transmission belt is wound around the first transmission pulley and the second transmission pulley.

12. The triaxial motion device as claimed in claim 1, wherein the second driving shaft of the second power source is connected with the third base through a second transmission unit; the second transmission unit has a third transmission pulley, a fourth transmission pulley and a second transmission belt; the third transmission pulley is disposed on a top end of the second base and connected with the second driving shaft coaxially; the fourth transmission pulley is disposed on a bottom end of the second base and connected with the third base; the second transmission belt is wound around the third transmission pulley and the fourth transmission pulley.

13. The triaxial motion device as claimed in claim 1, wherein an included angle between the first arm and the second arm is ranged from 90 to 180 degrees; the first power source and the second power source are both disposed on the second arm.

\* \* \* \* \*